United States Patent [19]

Bergström

[11] Patent Number: 5,968,966
[45] Date of Patent: Oct. 19, 1999

[54] METHOD AND COMPOSITIONS FOR THE TREATMENT OF RENAL FAILURE

[75] Inventor: Jonas Bergström, Stockholm, Sweden

[73] Assignee: Baxter International Inc., Deerfield, Ill.

[21] Appl. No.: 08/953,797

[22] Filed: Oct. 9, 1997

Related U.S. Application Data

[62] Division of application No. 08/742,018, Oct. 31, 1996.

[51] Int. Cl.$^6$ .................................................. A01N 43/50
[52] U.S. Cl. ........................... 514/400; 514/396; 514/399
[58] Field of Search ...................................... 514/399, 400

[56] References Cited

U.S. PATENT DOCUMENTS 4,446,149   5/1984   Nagai .

FOREIGN PATENT DOCUMENTS

WO 95/29675   4/1995   WIPO .
WO 95/29675   9/1995   WIPO .

OTHER PUBLICATIONS

Bergstrom, J. et al., "Intra cellular free amino–acids in muscle tissue of pateints with chronic uremia effect of peritoneal dialysis and infusion of essential amino–aids", Clin. Sci. Mol. Med. 54(1), pp. 51–60, 1978, see abstract.

*Primary Examiner*—Dwayne C. Jones
*Attorney, Agent, or Firm*—Thomas S. Borecki; Charles R. Mattenson; Robert M. Barrett

[57] ABSTRACT

Methods and compositions for treating renal failure patients are provided. Pursuant to the present invention, a renal failure patient is provided with an intravenous or dialysis solution that includes a therapeutically effective amount of L-carnosine. In part, the L-carnosine will prevent the renal failure patient from developing L-carnosine deficiency.

8 Claims, 2 Drawing Sheets

METHOD AND COMPOSITIONS FOR THE TREATMENT OF RENAL FAILURE

This is a division of application Ser. No. 08/742,018, filed on Oct. 31, 1996.

BACKGROUND OF THE INVENTION

The present invention relates generally to the treatment of diseases. More specifically the present invention relates to methods and compositions for the treatment of renal disease.

Of course, due to a variety of diseases and insults renal failure can occur in a patient. Acute renal failure can result from: direct renal tubular injury; renal ischemic; and intra-tubular obstruction. Renal failure results in diminished glomerular filtration and reduced secretion of metabolic waste products, water and electrolytes. Resultant fluid overload, electrolyte imbalances, and uremic syndrome can result in organ dysfunction ultimately resulting in death.

It is known to use dialysis to support a patient whose renal function is decreased to a point where the kidneys no longer sufficiently function. Dialysis provides a method for supplementing and replacing renal function in certain patients. Two principal dialysis methods are utilized: hemodialysis dialysis; and peritoneal dialysis.

In hemodialysis, the patients blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semi-permeable membrane. The peritoneum is the membranous lining of the abdominal cavity that due to a large number of blood vessels and capillaries is capable of acting as a natural semi-permeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows the proper acid-base electrolyte and fluid balance to be returned to the blood and the dialysis solution is simply drained from the body cavity through the catheter.

Although the use of dialysis, and other methods for treating patients with renal disease, provide treatments that allow patients with renal failure to survive, currently used compositions and methods may not provide all necessary therapeutic agents necessary to address renal failure.

SUMMARY OF THE INVENTION

The present invention provides methods and compositions for treating renal failure patients. Pursuant to the present invention, a renal failure patient is provided with an intravenous or dialysis solution that includes a therapeutically effective amount of L-carnosine. In part, the L-carnosine will prevent the renal failure patient from developing L-carnosine deficiency.

To this end, in an embodiment, the present invention provides a method for treating patients with renal failure comprising the step of providing through a non-oral method a therapeutically effective amount of a composition including L-carnosine.

In an embodiment, the composition is administered to the patient intravenously.

In an embodiment, the composition is administered to the patient through the peritoneal cavity.

In an embodiment, the composition includes amino acids.

In an embodiment, the composition includes carbohydrates.

In an embodiment, the composition includes fats.

In a further embodiment, the present invention provides a method for treating a patient receiving dialysis comprising the steps of administering to the patient a therapeutically effective amount of a composition including L-carnosine.

In an embodiment, the composition is administered to the patient parenterally.

In an embodiment, the composition is administered to the patient through the peritoneal cavity.

In an embodiment, the patient is receiving hemodialysis.

In an embodiment, the patient is receiving peritoneal dialysis.

In a still further embodiment, the present invention provides a peritoneal dialysis solution including a therapeutically effective amount of L-carnosine.

In an embodiment, the solution includes approximately 1.0 to about 40.0 mmol/L of L-carnosine.

In an embodiment, the peritoneal dialysis solution includes an osmotic agent chosen from the group consisting of dextrose, amino acids, polypeptides, polyglucose, and glycerol.

In an embodiment the peritoneal dialysis solution includes:
  approximately 100 to about 150 mEq/L sodium;
  approximately 70 to about 140 mEq/L chloride;
  approximately 0.0 to about 45.0 mEq/L lactate;
  approximately 0.0 to about 45.0 mEq/L bicarbonate;
  approximately 0.0 to about 4.0 mEq/L calcium; and
  approximately 0.0 to about 4.0 mEq/L magnesium.

In yet a further embodiment, the present invention provides a peritoneal dialysis solution comprising:
  approximately 1.0 to about 40.0 L-carnosine mmol/L;
  approximately 0 to about 300 dextrose mmol/L;
  approximately 100 to about 150 sodium mmol/L;
  approximately 70 to about 140 chloride mEq/L;
  approximately 0.0 to about 45.0 lactate mEq/L;
  approximately 0.0 to about 45.0 B-carbonate mEq/L;
  approximately 0.0 to about 4.0 calcium mEq/L; and
  approximately 0.0 to about 4.0 magnesium mEq/L.

An advantage of the present invention is to provide an improved method for treating renal failure patients.

Another advantage of the present invention is to provide an improved composition for treating renal failure patients.

Furthermore, an advantage of the present invention is to provide an improved peritoneal dialysis solution for patients with renal failure.

Still further, an advantage of the present invention is to provide an improved method for providing peritoneal dialysis to a patient.

Further, an advantage of the present invention is to provide a method for preventing L-carnosine deficiency in a renal failure patient.

Moreover, an advantage of the present invention is to normalize low muscle carnosine concentrations typically found in renal failure patients.

Additional features and advantages of the present invention are described in, and will be apparent from, the detailed description of the presently preferred embodiments and the figures.

DETAILED DESCRIPTION OF THE PRESENTLY PREFERRED EMBODIMENTS

Figure 1A:
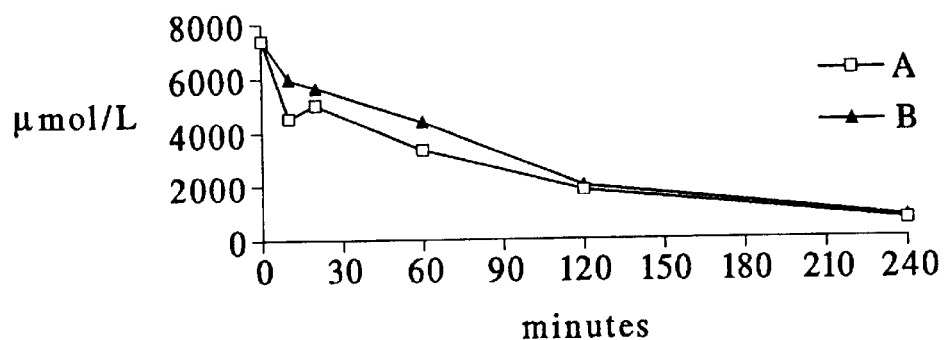
FIGS. 1A and 1B illustrate graphically, L-carnosine levels in dialysis solution over time for a dialysis solution containing L-carnosine at 8 mmol/L.

The present invention provides improved methods and compositions for the treatment of renal failure. Pursuant to the present invention, renal failure patients are provided, through a dialysis solution or intravenously, with a source of L-carnosine. It has been found that the L-carnosine will prevent and/or treat L-carnosine deficiency. In this regard it has been surprisingly found that L-carnosine can be effectively transferred from a peritoneal dialysis solution in the patient's peritneum to plasma and then taken up by tissue.

The dipeptide L-carnosine (β-alanyl-L-histidine) is one of the major non-protein-nitrogen constituents in skeletal muscles. In skeletal muscles it appears that L-carnosine functions as an intracellular buffer. Additionally, L-carnosine is an activator of ATP and a body store of histidine.

It has been recently demonstrated that L-carnosine acts as a natural antioxidant. In this regard, L-carnosine scavenges free-radicals, decreases membrane lipid oxidation and elicits membrane-protective and immune-modulating effects.

It has been found that in patients with chronic renal failure, the intracellular muscle concentration of L-carnosine is significantly reduced. For example, in acidotic hemodialysis patients intracellular muscle concentrations of L-carnosine are reduced by approximately 46% (see Experiment No. 1 infra). The inventor hypothesizes that the reduction of L-carnosine, and the reduced buffer capacity and other metabolic effects caused by such a reduction, can result in muscle fatigue, impaired immune response, increased lipid peroxidation and the risk of atherosclerosis. It has been surprisingly found that plasma levels of L-carnosine can be increased through the effective transfer of L-carnosine from a peritoneal dialysis solution containing same to plasma and from plasma to the muscle tissues.

Accordingly, pursuant to the present invention renal failure patients are provided with intravenous or peritoneal dialysis solutions that include a therapeutically effective amount of L-carnosine.

In an embodiment of the present invention, a patient receiving peritoneal dialysis is infused with a dialysis solution containing L-carnosine. As previously noted, it has been found that when L-carnosine is added to a dialysis fluid, it is absorbed from the peritoneal cavity. As noted below, in hemodialysis patients and other nondialysized renal failure patients, L-carnosine may be given intravenously with or without other nutrients.

Pursuant to the present invention, in a peritoneal dialysis solution preferably approximately 1.0 to about 40.0 mmol/L of L-carnosine will be present.

In accordance with the present invention, any of a variety of different peritoneal dialysis solutions can be used as long as they include L-carnosine. For example, the peritoneal dialysis solution can include any known osmotic agent, e.g., dextrose, glycerol, polyglucose, polypeptides, and amino acids.

In an embodiment, the peritoneal dialysis solution includes:

approximately 100 to about 150 mEq/L sodium;
approximately 70 to about 140 mEq/L chloride;
approximately 0.0 to about 45.0 mEq/L lactate;
approximately 0.0 to about 45.0 mEq/L bicarbonate;
approximately 0.0 to about 4.0 mEq/L calcium;
approximately 0.0 to about 4.0 mEq/L magnesium;
approximately 1.0 to about 40.0 L-carnosine mmol/L; and
approximately 0.0 to about 300 dextrose mmol/L.

In another embodiment, the peritoneal dialysis solution includes:

approximately 100 to about 150 mEq/L sodium;
approximately 70 to about 140 mEq/L chloride;
approximately 0.0 to about 45.0 mEq/L lactate;
approximately 0.0 to about 45.0 mEq/L bicarbonate;
approximately 0.0 to about 4.0 mEq/L calcium;
approximately 0.0 to about 4.0 mEq/L magnesium;
approximately 1.0 to about 40.0 L-carnosine mmol/L; and
approximately 0.0 to about 300 mmol/L other osmotic agent.

As noted above, it is also possible to practice the present invention by administering to a renal failure patient an intravenous solution containing L-carnosine.

In such an intravenous solution preferably the solution will include approximately 1.0 to about 80 mmol/L of L-carnosine. The solution would be administered approximately 1 to 3 times per day.

Examples of intravenous solutions containing L-carnosine include:

approximately 1 to about 80 mmol/L L-carnosine;
approximately 0 to about 200 mEq/L sodium;
approximately 0 to about 100 mEq/L potassium;
approximately 0 to about 300 mEq/L chloride;
approximately 0 to about 10 mEq/L calcium;
approximately 0 to about 10 mEq/L magnesium;
approximately 0 to about 20 mmol/L phosphate;
approximately 0 to about 100 mEq/L bicarbonate;
approximately 0 to about 100 mEq/L lactate;
approximately 0 to about 100 mEq/L acetate;
approximately 0 to about 150 g/L amino acids;
approximately 0 to about 100 g/L dipeptides; and
approximately 0 to about 300 g/L lipids.

By way of example, and not limitation, experiments with respect to the present invention will now be given:

EXPERIMENT 1

Muscle (m-) carnosine (CARN) and histidine (HIS) levels (sampled by percutaneous needle biopsy of quadriceps femoris, analysis by HPLC) and plasma (p-) HIS in 9 hemodialysis patients before and after correction of the acidosis over a 6 months period and in 15 healthy controls were taken. The patients were in good clinical condition without signs of malnutrition.

Results are presented as means±S.D.

|  | St.HCO3 (mmol/L) | P-HIS (µmol/L) | m-HIS (µmol/L) | m-CARN (µmol/L i.c.H2O) |
|---|---|---|---|---|
| Before | 20.3 ± 1.3 | 86 ± 22 | 467 ± 171 a | 4697 ± 1681 a |
| After | 25.9 ± 1.8 | 65 ± 7 a,b | 522 ± 169 | 6122 ± 2408 a,b |
| Controls |  | 81 ± 8 | 628 ± 138 | 8621 ± 1707 | a=sign.diff from controls, b=sign.diff before-after

The sampling demonstrated that muscle carnosine concentrations, which in the acidotic pat, was reduced by 46% compared to the controls. These concentrations although they increased significantly after acidosis correction did not reach normal levels. Plasma HIS fell after acidosis correction and the i.c/e.c gradient of histidine increased from 5.4±1.8 to 7.9±1.8.

The observations suggest that acidosis has an impact of histidine and carnosine metabolism in uremia. The inventor speculates that low muscle carnosine with reduced i.c. buffer capacity may be involved in muscle dysfunction of uremic patients and that acidosis may have a role in this context.

EXPERIMENT 2

The aim of the study was to test in pilot experiments the uptake of L-carnosine from dialysis fluid to plasma in rats.

Experimental animals: Male Sprague-Dawley rats, weighing about 300 g.

Peritoneal Dialysis solutions used:
I: Dianeal® 1.36% (available from Baxter Healthcare of Deerfield, Ill.)+L-carnosine 8 mmol/L
II: Dianeal® 1.36% (available from Baxter Healthcare of Deerfield, Ill.)+L-carnosine 16 mmol/L Intraperitoneal fill volume: 25 ml Dialysate samples: (0.2 ml); 0, 10, 20, 60, 120, 240 min.

Blood samples: (0.2 ml); 0, 60, 120, 240 min.

Analyses: L-carnosine and L-histidine in dialyzate and plasma.

Figure 1B:
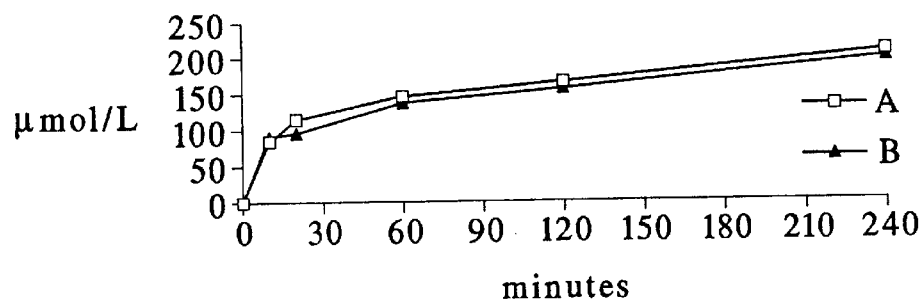
Figure 2A:
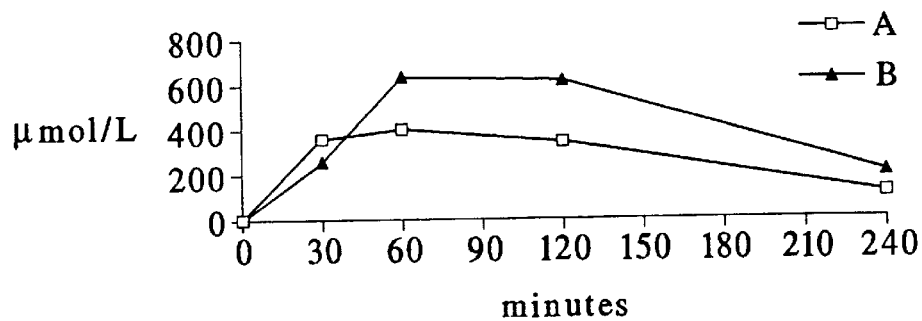
FIGS. 2A and 2B illustrate graphically, plasma-carnosine levels over time in two rats infused with the dialysis solution of FIGS. 1A and 1B.
Figure 2B:
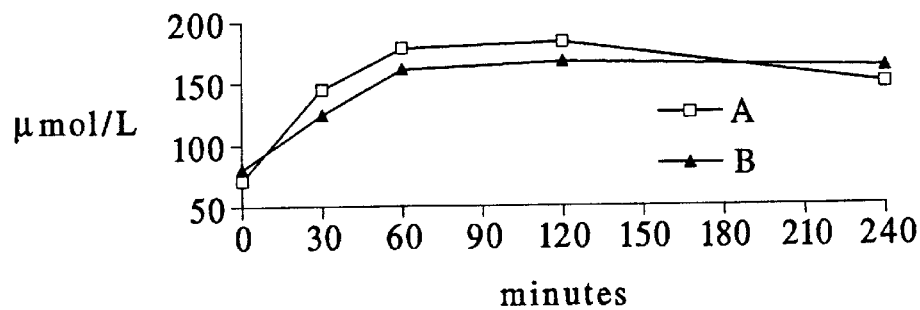

Results:

FIGS. 1A, 1B, 2A and 2B graphically illustrate the results in rats A and B, receiving 25 ml peritoneal dialysis solution containing L-carnosine 8 mmol/L. There was a rapid fall in L-carnosine concentration in the dialyzate along with a continuous increase in L-histidine concentration up to a level of 213 µmol/L. At the end of the dwell (240 min) the dialyzate concentration of L-carnosine was about 10% of the original concentration. Plasma levels of L-carnosine increased from zero to 432–677 µmol/L after 60 min, then gradually falling to 113 and 224 µmol/L after 240 min. Plasma L-histidine increased from 72 and 80 µmol/L to 182 and 166 µmol/L after 120 min and 146 and 160 µmol/L, respectively after 240 min.

Figure 3A:
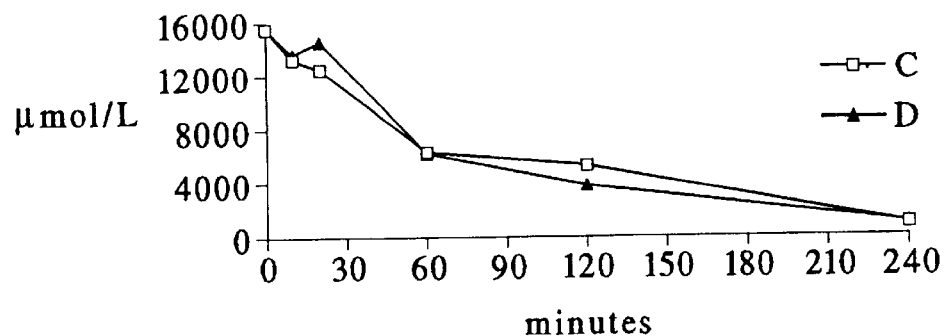
FIGS. 3A and 3B illustrate graphically, L-carnosine levels in dialysis solution over time for a dialysis solution containing L-carnosine at 16 mmol/L.
Figure 3B:
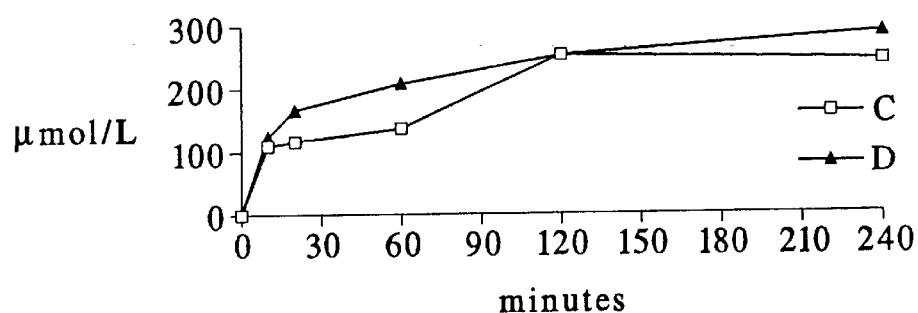
Figure 4A:
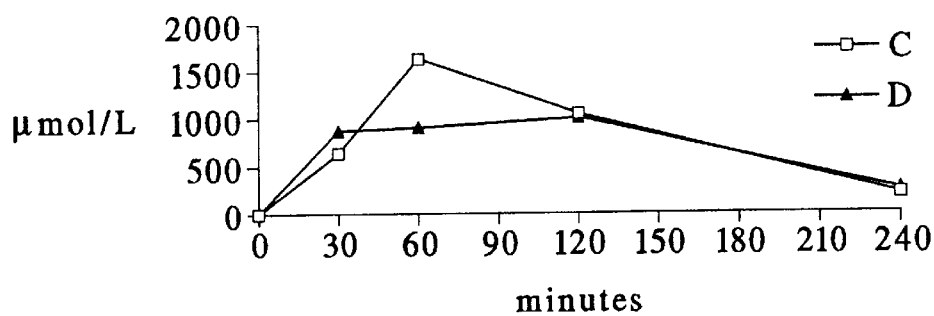
FIGS. 4A and 4B illustrate graphically, plasma-carnosine levels over time in two rats infused with the dialysis solution of FIGS. 3A and 3B.
Figure 4B:
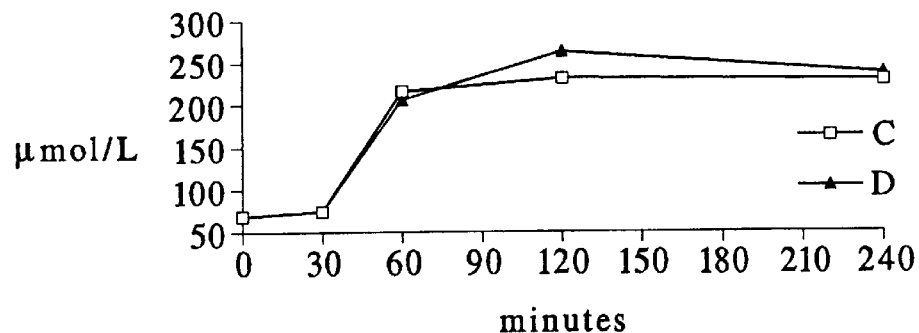

FIGS. 3A, 3B, 4A and 4B graphically illustrate the results in rats C and D, receiving 25 ml peritoneal dialysis solution containing L-carnosine 16 mmol/L. The pattern was similar as for rats A and B, with an initial rapid fall in L-carnosine concentration. At the end of the dwell the concentration was less than 10% of the original concentration. Dialyzate L-histidine increased gradually to reach 297 µmol/L. Plasma L-carnosine concentration were approximately twice as high as the concentration in rats A and B and were also higher (233 and 245 µmol/L) at the end of the dwell. Plasma L-histidine increased and plateaued around 230–270 µmol/L.

It was determined that L-carnosine in peritoneal dialysis fluid is absorbed to 90% or more. Of about 360 µmol absorbed from a solution containing L-carnosine 16 mmol/L, only a small part (<5%) accumulates in extracellular fluid (assumed to be 20% of the body weight). The increase in L-histidine in dialyzate and plasma indicates that L-carnosine is metabolized into its constituent amino acids.

However, since the increase in histidine concentration is small, the results suggest that most of the absorbed L-carnosine is taken up unmodified by skeletal muscle and other body cells. Hence, it should be feasible to correct intracellular L-carnosine depletion by adding L-carnosine to the dialysis fluid.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for treating patients with chronic renal failure comprising the step of providing, through a non-oral method, selected from the group consisting of intravenously and through the peritoneal cavity, a therapeutically effective amount of a composition comprising L-carnosine.

2. The method of claim 1 wherein the composition includes a source of amino acids.

3. The method of claim 1 wherein the composition includes carbohydrates.

4. The method of claim 1 wherein the composition includes fats.

5. A method for treating a patient receiving dialysis comprising the steps of administering to the patient a therapeutically effective amount of a composition comprising L-carnosine through a non-oral method, selected from the group consisting of intravenously and through the peritoneal cavity.

6. The method of claim 5 wherein the patient is receiving hemodialysis.

7. The method of claim 5 wherein the patient is receiving peritoneal dialysis.

8. The method of claim 5 wherein the patient is receiving a peritoneal dialysis solution containing the therapeutically effective amount of the composition containing L-carnosine and an osmotic agent chosen from the group consisting of dextrose, amino acids, polypeptides, polyglucose, and glycerol.

* * * * *